(12) United States Patent
Hsu et al.

(10) Patent No.: US 8,409,810 B2
(45) Date of Patent: Apr. 2, 2013

(54) PLATELET AGGREGATION ASSAYS USING A CD40L-BINDING AGENT

(75) Inventors: Yen-Ming Hsu, Lexington, MA (US); Lihe Su, Reading, MA (US)

(73) Assignee: Biogen Idec Ma Inc., Cambridge, MA (US)

( * ) Notice: Subject to any disclaimer, the term of this patent is extended or adjusted under 35 U.S.C. 154(b) by 383 days.

(21) Appl. No.: 12/093,658

(22) PCT Filed: Nov. 17, 2006

(86) PCT No.: PCT/US2006/044840
§ 371 (c)(1),
(2), (4) Date: May 14, 2009

(87) PCT Pub. No.: WO2007/059332
PCT Pub. Date: May 24, 2007

(65) Prior Publication Data
US 2009/0220998 A1    Sep. 3, 2009

Related U.S. Application Data

(60) Provisional application No. 60/737,488, filed on Nov. 17, 2005, provisional application No. 60/804,843, filed on Jun. 15, 2006.

(51) Int. Cl.
*G01N 33/53* (2006.01)
*A61K 35/14* (2006.01)
*A61K 38/36* (2006.01)
*C07K 16/00* (2006.01)

(52) U.S. Cl. ...... 435/7.1; 424/532; 514/13.8; 530/388.7

(58) Field of Classification Search .......... None
See application file for complete search history.

(56) References Cited

U.S. PATENT DOCUMENTS

| 3,694,161 A | 9/1972 | Kleszynski et al. |
| 5,951,951 A | 9/1999 | Lane et al. |
| 6,500,630 B2 | 12/2002 | Conover et al. |
| 2006/0149041 A1 * | 7/2006 | Silence ............ 530/388.25 |

FOREIGN PATENT DOCUMENTS

| EP | 0661383 | 7/1995 |
| EP | 1530047 | 5/2005 |
| WO | WO 02/078743 | 10/2002 |
| WO | 02089657 A2 | 11/2002 |
| WO | WO 03/040691 | 5/2003 |
| WO | WO 03/055516 | 7/2003 |

OTHER PUBLICATIONS

Koyama et al., Thrombophilia Associated With Anti-CD154 Monoclonal Antibody Treatment and Its Prophylaxis in Non Human Primates. Transplantation, 77, 460-462, 2004.*
Zucker M., Platelet Aggregation Measured by the Photometric Method., Methods in Enzymol. 169, 117-133, 1989.*
Henn et al., "The inflammatory action of CD40 ligand (CD154) expressed on activated human platelets is temporally limited by coexpressed CD40," *Blood*, 98(4):1047-1054 (2001).
Langer et al., "The role of CD40 in CD4OL- and antibody-mediated platelet activation," *Thrombosis Haemostasis*, 93(6):1137-1146 (2005).
MEDLINE On-line Abstract Accession No. 2004077257 of Koyama et al., "Thrombophilia associated with anti-CD154 monoclonal antibody treatment and its prophylaxis in nonhuman primates," *Transplantation*, 77(3):460-462 (2004).
Xu et al., "Human platelets activate porcine endothelial cells through a CD154-dependent pathway," *Transplantation*, 72(11):1858-1861 (2001).

* cited by examiner

*Primary Examiner* — Elly-Gerald Stoica
(74) *Attorney, Agent, or Firm* — Lando & Anastasi LLP

(57) ABSTRACT

The present invention provides methods of determining platelet aggregation, methods of determining susceptibility to clotting upon administration of a CD40L-binding moiety, and kits related thereto.

28 Claims, 4 Drawing Sheets

PLATELET AGGREGATION ASSAYS USING A CD40L-BINDING AGENT

RELATED APPLICATIONS

This application is the National Stage of International Application No. PCT/US2006/044840, which claims the benefit of U.S. Provisional Application No. 60/737,488, filed Nov. 17, 2005, and U.S. Provisional Application No. 60/804,843, filed Jun. 15, 2006. The contents of all of these prior applications are incorporated herein by reference in their entirety.

FIELD OF THE INVENTION

The present invention is directed, in part, to methods of determining platelet aggregation, methods of determining susceptibility to clotting upon administration of an anti-CD40L antibody, and kits related thereto.

BACKGROUND OF THE INVENTION

Thromboembolic complications (TEC) have been observed in some clinical trials of anti-CD40L (CD40L is abbreviated for CD40 ligand, also known as CD 154) antibody, in particular, humanized monoclonal antibody directed against CD40L. Known to be expressed by activated T cells, CD40L was also shown to be present on the surface of activated human platelets and may play a role in endothelial cell activation in vitro (Henn et al., Nature, 1998, 391, 591-594). However, the role of the CD40/CD40L pathway in regulating coagulation in vivo at the level of platelet/endothelial cell interaction is still undefined.

CD40L is a type II membrane protein first described to be expressed on activated T cells. The interaction of CD40L with its receptor, CD40, is critical for B cell differentiation, proliferation, and immunoglobulin (Ig) isotype switching induced by helper T cells (Foy et al., Annu. Rev. Immunol., 1996, 14, 591-617; and van Kooten et al., J. Leukoc. Biol., 2000, 67, 2-17). The involvement of the CD40/CD40L pathway in the interaction of platelets with endothelial cells has recently been described (Henn et al., Nature, 1998, 391, 591-594). Under normal conditions, CD40L is stored in platelets. Upon activation, CD40L is translocated to the surface of platelets accompanied by surface appearance of CD63, P-selectin, and several other proteins, as well as release of soluble mediators from intra-platelet granules (Murano G., Basic Concepts of Hemostasis and Thrombosis, 1980, Boca Raton, Fla., CRC Press, Inc.). Hence, CD40L may play a role in procoagulant activity.

Elevated levels of soluble CD40L (sCD40L) have been found in the blood of lupus patients (Kato et al., J. Clin. Invest., 1999, 104, 947-955; and Vakkalanka et al., Arthritis Rheum., 1999, 42, 871-881). Rheumatoid factor (RF), an autoantibody to the Fc portion of Ig, is often detected in the sera of patients with autoimmune disorders (Mageed et al., Ann. N.Y. Acad. Sci., 1997, 815, 296-311). Additionally, the administration of anti-CD40L antibody could result in the production of antibodies directed against anti-CD40L antibody.

SUMMARY OF THE INVENTION

The present invention provides methods of assaying platelet aggregation comprising contacting platelets with a platelet activating agent, contacting the activated platelets with a CD40L-binding moiety, and contacting the activated platelets with a cross-linking agent, wherein aggregation is quantified by sedimentation of platelets. The CD40L-binding moiety and the cross-linking agent are not a preformed immune complex. The platelet activating agent is selected from adenosine diphosphate (ADP), collagen, thrombin, thromboxane, neutrophil elastase, p-selectin, and convulxin. The platelets can be obtained from platelet rich plasma (PRP). In some embodiments, the CD40L-binding moiety is an anti-CD40L antibody, such as hu5c8. The cross-linking agent is selected from soluble CD40L (sCD40L), anti-human IgG antibody, anti-hFc antibody, RF, Fc receptor-positive accessory cell, soluble protein A, and soluble human Fc receptor. The ratio of anti-CD40L antibody to sCD40L can be 1:1000 to 1000:1, 1:500 to 500:1, or 3:2.

The present invention also provides methods of assaying platelet aggregation comprising activating platelets by ADP, contacting the activated platelets with an anti-CD40L antibody, and contacting the activated platelets with sCD40L or anti-hFc antibody, wherein sedimented platelets is indicative of aggregation of the platelets. The anti-CD40L antibody and sCD40L are not a preformed immune complex.

The present invention also provides methods of determining whether an individual is susceptible to clotting upon administration of a CD40L-binding moiety comprising removing platelets from the human, contacting the platelets with a platelet activating agent, contacting the activated platelets with the CD40L-binding moiety, contacting the activated platelets with a cross-linking agent, and determining the presence or absence of platelet aggregation, wherein 70% or greater platelet aggregation is indicative of susceptibility to clotting. The CD40L-binding moiety and the cross-linking agent are not a preformed immune complex. The platelet activating agent is selected from ADP, collagen, thrombin, thromboxane, neutrophil elastase, p-selectin, and convulxin. The platelets can be obtained from platelet rich plasma (PRP). In some embodiments, the CD40L-binding moiety is an anti-CD40L antibody, such as hu5c8. The cross-linking agent is selected from sCD40L, anti-human IgG antibody, anti-hFc antibody, RF, Fc receptor-positive accessory cell, soluble protein A, and soluble human Fc receptor. The ratio of anti-CD40L antibody to sCD40L can be 1:1000 to 1000:1, 1:500 to 500:1, or 3:2.

The present invention also provides methods of determining whether a human is susceptible to clotting upon administration of an anti-CD40L antibody comprising removing platelets from the human, activating the platelets with ADP, contacting the activated platelets with the anti-CD40L antibody, contacting the activated platelets with sCD4-L or anti-hFc antibody, and determining the presence or absence of platelet aggregation, wherein 70% or greater platelet aggregation is indicative of susceptibility to clotting. The anti-CD40L antibody and the cross-linking agent are not a preformed immune complex.

The present invention also provides kits comprising a platelet activating agent, a cross-linking agent, and, optionally, a CD40L-binding moiety. The platelet activating agent is selected from ADP, collagen, thrombin, thromboxane, neutrophil elastase, p-selectin, and convulxin. The CD40L-binding moiety can be an anti-CD40L antibody, such as hu5c8. The cross-linking agent is selected from sCD40L, anti-human IgG antibody, anti-hFc antibody, RF, Fc receptor-positive accessory cell, soluble protein A, and soluble human Fc receptor. The kit may further comprise at least one of a needle, a container for accepting blood, a container for accepting assay components, and instructions. In some embodiments, the container for accepting assay components is a cuvette.

DESCRIPTION OF EMBODIMENTS

Figure 1:
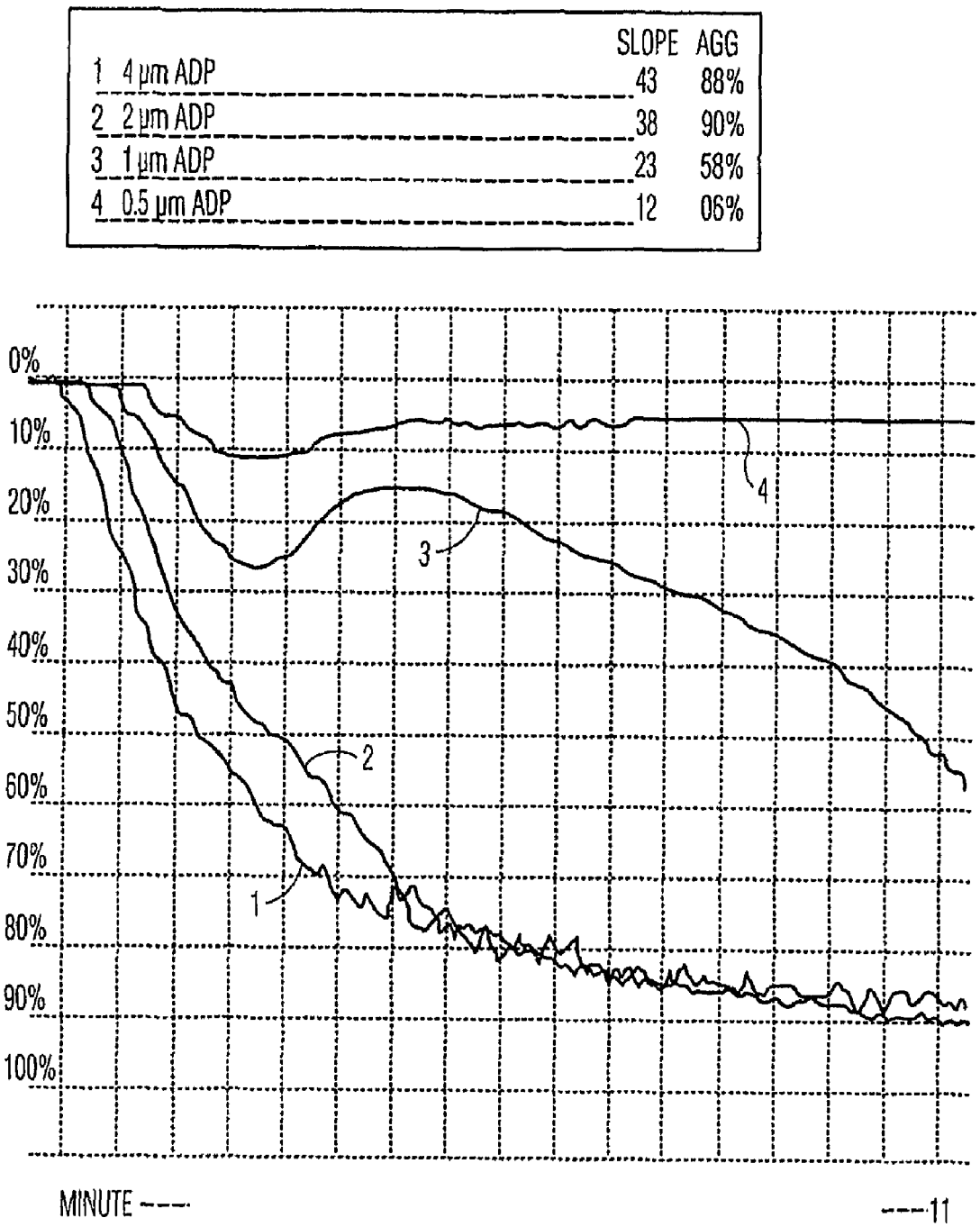
FIG. 1 shows Biodata 4-channel platelet aggregation profiler produced tracings depicting the percent of light transmitted through the samples as compared to the PRP control. The tracings are ended four minutes after the addition of sub-optimal quantities of ADP, and the final value considered to be the percent of platelets aggregated. An ADP titration is performed to determine the sub-optimal concentration of ADP for each PRP sample.

The present invention provides methods of assaying platelet aggregation, methods of determining whether a human is susceptible to clotting upon administration of a CD40L-binding moiety, and to kits that can be used in these methods.

In one aspect, the present invention provides methods of assaying platelet aggregation comprising contacting platelets with a platelet activating agent, contacting the activated platelets with a CD40L-binding moiety, and contacting the activated platelets with a cross-linking agent. Sedimented platelets is indicative of aggregation of the platelets. The CD40L-binding moiety and the cross-linking agent are not a preformed immune complex when they are added to the platelets. Sedimented platelets is indicative of aggregation of the platelets.

In some embodiments, the platelets are obtained from a mammal such as a human. Platelets can be present in PRP obtained from a human. Additionally, the platelets can be isolated from the PRP if so desired. In some embodiments, the platelets or PRP are obtained from a human prior to administration of a CD40L-binding moiety, such as an anti-CD40L antibody, to determine, for example, whether the human is at risk of clotting or platelet aggregation upon administration of the CD40L-binding moiety. Blood can be obtained from humans by widely known techniques. PRP can be separated from cellular components by commonly used separation techniques including, for example, centrifugation and the like. A typical platelet preparation is described in Example 2 below. Purification by Sepharose gel filtration column is described Fine et al., Am. J. Pathol., 1976, 84, 11-24, and in Example 3 below.

The platelets or PRP are contacted by a platelet activating agent. As used herein, the phrase "platelet activating agent" means any compound that can be used to sub-optimally activate a platelet. Sub-optimal activation of platelets is desired so as to be able to discern aggregation caused by the CD40L-binding moiety. For example, platelets can be contacted with an amount of a platelet activating agent to induce a threshold, or sub-optimal, amount of platelet aggregation. This amount of platelet aggregation should be less than the amount of aggregation induced by the CD40L-binding moiety, and may range from 0% aggregation to less than 70% aggregation, or any sub-range therewithin. Platelet activating agents are well known to the skilled artisan and include, but are not limited to, ADP, collagen, thrombin, thromboxane (TxA2, for example), human neutrophil elastase (HNE), p-selectin, convulxin, and the like.

The platelets are also contacted with a CD40L-binding moiety. As used herein, the phrase "CD40L-binding moiety" is any compound that contains a functional Fc antibody domain and which is also able to bind to CD40L. In some embodiments, the CD40L-binding moiety is an anti-CD40L antibody. As used herein, the phrase "anti-CD40L antibody" means any antibody, or fragment or mutant thereof, that is capable of binding CD40L and/or sCD40L and which is also capable of functionally interacting with the Fc receptor. Thus, in some embodiments, the anti-CD40L antibody comprises a fully intact Fc region. In other embodiments, the anti-CD40L antibody comprises a fully intact but modified Fc region, wherein the modification does not interfere with Fc receptor binding and/or signaling. In other embodiments, the anti-CD40L antibody comprises a mutant and/or shortened Fc region, wherein the mutation and/or shortening does not interfere with Fc receptor binding and/or signaling. Anti-CD40L antibodies are well known to the skilled artisan and include, for example, the hu5c8. Additional anti-CD40L antibodies include, but are not limited to, M90, M91, M92, IDEC 131, and AnCell anti-CD154 (also known as 24-31), as well as those disclosed in Gray et al., Seminars in Immunol, 1994, 6, 303-310 and Noelle, Immunity, 1996, 4, 415-419. In addition, CD40-Fc is a reagents capable of cross-linking CD40L.

The platelets are also contacted with a cross-linking agent. As used herein, the phrase "cross-linking agent" means any agent that can be used to cross-link CD40L-binding moieties. Suitable cross-linking agents are well known to the skilled artisan and include, but are not limited to, sCD40L, anti-human IgG antibodies, anti-hFc antibody, RF, Fc receptor-positive accessory cells, soluble protein A, and soluble human Fc receptors (such as FcγRI, FcγRII, FcγRIII, and FcRn). The ratio of CD40L-binding moiety to sCD40L, for example, is 1:1000 to 1000:1, 1:500 to 500:1, 1:100 to 100:1, 1:10 to 10:1, or 3:2.

Upon contacting platelets with platelet activating agent, CD40L-binding moiety, and a cross-linking agent, sedimentation of platelets is indicative of platelet aggregation. The lack of platelet sedimentation is indicative of a lack of platelet aggregation. In some embodiments, a negative control, or blank, may be used to establish a baseline or threshold amount of platelet aggregation. A test sample containing platelets, platelet activating agent, CD40L-binding moiety, and cross-linking agent can be assayed to determine the amount of platelet aggregation, and compared to the baseline platelet aggregation. Any difference in the amount of platelet aggregation between the test sample and the negative control can be indicative of platelet aggregation in the test sample. The assay can be carried out in any suitable container for accepting assay components such as, for example, a test tube, microfuge tube, or cuvette.

In another aspect, the present invention also provides methods of determining whether a human is susceptible to clotting upon administration of a CD40L-binding moiety. As stated above, thromboembolic complications, including clotting, have been observed upon administration of an anti-CD40L antibody to a human. Thus, in some instances, it is desirable to determine whether a human who is contemplating receiving an anti-CD40L antibody, or any other CD40L-binding moiety, is susceptible to establishing such complications upon treatment. Representative methods comprise removing platelets from the human, activating the platelets with a platelet activating agent as described above, contacting the activated platelets with a CD40L-binding moiety as described above, contacting the activated platelets with a cross-linking agent as described above, and determining the presence or absence of platelet aggregation. The CD40L-binding moiety and the cross-linking agent are not a preformed immune complex.

Platelet aggregation, and the presence or absence thereof, can be determined by numerous means known to those skilled in the art. For example, sedimentation of platelets, which is an indication of platelet aggregation, can be monitored as described in the Examples below. The amount of platelet aggregation can vary from sample to sample depending upon, for example, the CD40L-binding moiety and the platelets themselves. Where the amount of platelet aggregation is 70% or greater, or 75% or greater, or 80% or greater, or 85% or greater, or 90% or greater, or 95% or greater, it is indicative of susceptibility to clotting and/or thromboembolic complications. A human, who is contemplating receiving treatment with an anti-CD40L antibody, for example, and who tests positive (i.e., has greater than 70% platelet aggregation) in the assay method described herein (i.e., the human is susceptible to clotting) may contemplate alternate therapeutic regimens. Indeed, health care professionals may offer alternate therapies upon receiving a particular result in the assays described herein.

In another aspect, the present invention provides a kit comprising a platelet activating agent, a cross-linking agent, and, optionally, a CD40L-binding moiety. In some embodiments, the platelet activating agent is selected from ADP, collagen, thrombin, thromboxane, neutrophil elastase, p-selectin, and convulxin. In some embodiments, the CD40L-binding moiety is an anti-CD40L antibody, such as, for example, hu5c8. In some embodiments, the cross-linking agent is selected from sCD40L, anti-human IgG antibody, anti-hFc antibody, RF, Fc receptor-positive accessory cell, soluble protein A, and soluble human Fc receptor. The kit can also contain additional items such as, for example, needle, a container for accepting blood, a container for accepting assay components, and instructions for carrying out the methods described herein. In some embodiments, the container for accepting assay components is a cuvette.

In order that the invention disclosed herein may be more efficiently understood, examples are provided below. It should be understood that these examples are for illustrative purposes only and are not to be construed as limiting the invention in any manner.

EXAMPLES

Example 1

Reagents

Research-grade anti-CD40L antibody, recombinant sCD40L, and recombinant soluble CD40-IgG1 Fc fusion protein (CD40-Fc) were prepared at Biogen (Ferrant et al., Mol. Immunol., 2002, 39, 77-84). The control human IgG was a human IgG1 kappa purchased from Protos Immunoresearch (San Francisco, Calif.). The antibody to the Fc region of human IgG (anti-hFc) was an affinity purified mouse antihuman IgG Fc (Jackson ImmunoResearch, West Grove, Pa.). Rb779 is a rabbit antiserum raised against a peptide derived from the C-terminus of CD40L (Garber et al., J. Biol. Chem., 1999, 274, 33545-33550).

Example 2

Preparation of Platelet Rich Plasma (PRP) and Recovery of Platelets

All platelets used in the in vitro platelet aggregation experiments were isolated from healthy human volunteers who denied ingesting aspirin or aspirin containing compounds within 10 days. Aggregation assays were performed on PRP. Approximately 50 mL of whole blood was collected in aliquots in 4.5 mL vacutainer tubes containing 0.5 mL of 3.8% sodium citrate. PRP was prepared by centrifuging the anticoagulated blood at 200 g for 10 minutes and harvesting the supernatant.

Example 3

Western Blotting

Western blotting for CD40L was performed on purified platelets prepared as following. A total of 50 mL of whole blood was collected in aliquots in 4.5 mL vacutainer tubes containing 0.5 mL of 3.8% sodium citrate. PRP was prepared by centrifuging the blood for 20 minutes at 180 g. The collected PRP supernatant was loaded onto a Sepharose CL2B (Pharmacia, Peapack, N.J.) gel filtration column, previously equilibrated with two column volumes of phosphate buffered saline (PBS). The platelets were eluted and washed with PBS. Western blotting was performed to quantitate the amount of CD40L present in platelets. Briefly, platelets were treated with Laemmli sample buffer and the proteins resolved by electrophoresis through a gradient sodium dodecyl sulfate-polyacrylamide gel (Laemmli, Nature, 1970, 227, 680-685). The proteins were transferred to nitrocellulose (Towbin et al., Proc. Natl. Acad. Sci. U.S.A., 1979, 76, 4350-4354) and the membrane blotted with Rb779, a rabbit antiserum raised against a peptide derived from the C-terminus of human CD40L protein (Garber et al., J. Biol. Chem., 1999, 274, 33545-33550). The bound antibody was detected by a goat anti-rabbit antiserum conjugated to horseradish peroxidase (HP). Serial dilutions of recombinant sCD40L were evaluated in parallel with the platelet-derived protein samples. The amount of CD40L in the platelet samples was estimated by comparison to the recombinant sCD40L standard.

Platelets were incubated with a biotin-conjugated anti-CD40L antibody to determine whether CD40L is present on the surface of platelets. PRP was incubated with or without 10 μM ADP for 1, 10, 20, 40, or 60 minutes and then incubated with biotin-conjugated anti-CD40L antibody. Unbound antibody was removed from the platelets by washing with PBS. The amount of anti-CD40L antibody bound to the platelets was determined by western blotting using HRP-conjugated streptavidin. The specific binding of biotin-conjugated anti-CD40L antibody to the platelets was verified by preincubating the antibody with recombinant sCD40L.

Example 4

Platelet Aggregation Assay

The Biodata 4-channel platelet aggregation profiler (PAP-4; Biodata Corp., Hatboro, Pa.) was blanked using a cuvette containing only platelet poor plasma (PPP). A 350 µL aliquot of PRP, containing approximately 2 to $5 \times 10^8$/mL platelets, was added to a cuvette containing a stir bar. Anti-CD40L antibody, human IgG, normal human serum, CD40-Fc, or anti-hFc were added in a total volume of 100 µL. The loaded cuvette was placed in the machine and the reaction components mixed prior to the addition of ADP.

Aggregation was initiated with the addition of sub-optimal concentration of ADP in 50 µL (final concentration varies for each individual sample). The aggregation profiler has four ports, which can run simultaneously. An aggregation tracing was generated for each sample for four minutes following the addition of ADP. At the end of the tracing, the instrument calculates the percentage of aggregation by comparing the transmission of light through the sample to the transmission of light through the PPP blank. A tracing representative of a typical ADP titration is shown in FIG. 1. A titration was performed at the beginning of each experiment, and subsequent runs were performed at a suboptimal ADP concentration.

Example 5

Expression of CD40L on the Surface of Activated Platelets

Figure 2:
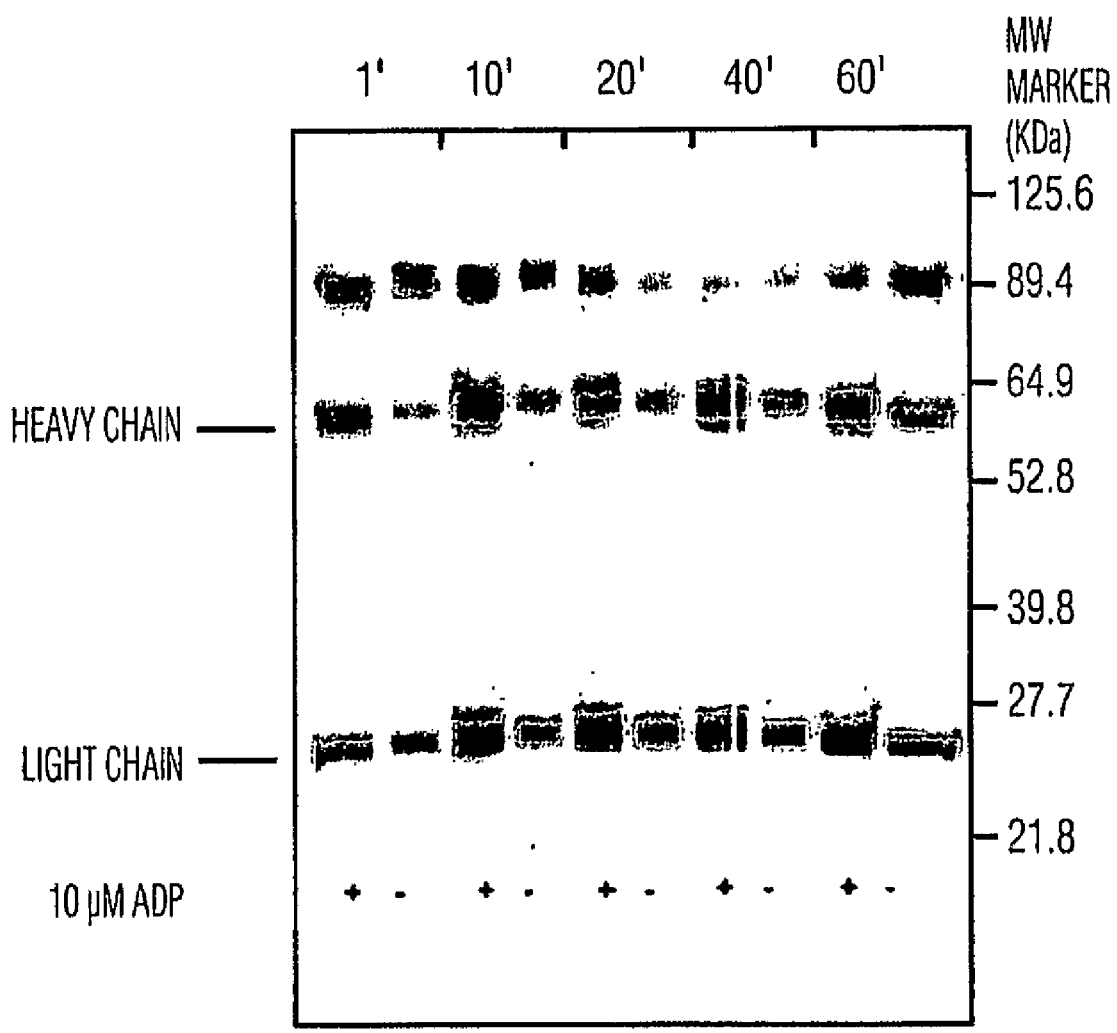
FIG. 2 shows that activated platelets express surface CD40L. Human platelets were incubated with or without 10 µM ADP for 1, 10, 20, 40, or 60 minutes. As CD40L on the platelet surface is capable of interacting with biotinylated anti-CD40L antibody, the activation induced increase of CD40L on the platelet surface is quantified by western blotting for biotinylated anti-CD40L antibody associated with activated platelets.

Expression of CD40L was readily detected in lysates prepared from human platelets (data not shown). To determine whether CD40L is expressed on resting and/or activated platelets, platelets were incubated with biotin-conjugated anti-CD40L antibody and the presence of surface CD40L was determined by quantifying the bound biotinylated anti-CD40L antibody. Surface expression of CD40L was evaluated after 1, 10, 20, 40, and 60 minutes of incubation with or without 10 µM ADP. Surface expression of CD40L was detectable on ADP-activated platelets as early as one minute after activation and increased over time (FIG. 2). The binding of biotin-conjugated anti-CD40L antibody is specific for CD40L, as preincubation of biotin-conjugated anti-CD40L antibody with sCD40L inhibited binding to activated platelets (data not shown). The amount of surface CD40L detected on unactivated ("resting") platelets also increased over time. This phenomenon is likely attributable to the basal level of platelet activation under our experimental conditions.

Notwithstanding, the amount of surface CD40L expressed on ADP-treated platelets was consistently higher than that of the matched untreated controls. These results are consistent with the notion that CD40L is normally sequestered inside of platelets and is translocated to the surface upon activation. Furthermore, the binding of biotin-conjugated anti-CD40L antibody confirms that anti-CD40L antibody recognizes the CD40L molecules present on the platelet surface.

Example 6

Estimation of the Amount of CD40L in the Platelet Compartment

As CD40L expressed on the surface of activated platelets can be recognized by anti-CD40L antibody, it is important to estimate the size of this potential "sink" for anti-CD40L antibody. Using a western blotting method, the amount of CD40L in platelets was compared to known amounts of a recombinant sCD40L standard. The amount of CD40L in one million platelets is estimated to be approximately 80 pg. Each milliliter of freshly drawn blood contains about 300 million platelets, and an average person has a total blood volume of about 5 L. By calculation, approximately 120 µg of CD40L is present in the platelet compartment of an average individual.

Example 7

Effect of Research-Grade Anti-CD40L antibody on Platelet Aggregation

To determine whether the interaction of anti-CD40L antibody with CD40L expressed on activated platelets influences the hemostatic cascade, the aggregation of healthy human platelets in the presence of research-grade anti-CD40L antibody was examined. Research-grade anti-CD40L antibody did not affect the aggregation of ADP-activated platelets over a wide range of ADP concentrations (Tables 1 through 3). Resting platelets were also not affected by anti-CD40L antibody (Tables 1 and 3-5). As expected, control human IgG antibody (Tables 2 and 3) did not affect platelet aggregation. CD40-Fc was evaluated to determine whether the binding of a dimeric receptor protein to the CD40L expressed on the surface of platelets would influence aggregation. CD40-Fc did not affect platelet aggregation (Table 4).

Example 8

Effect of Cross-Linked Anti-CD40L Antibody on Platelet Aggregation

Anti-CD40L Antibody Cross-Linked by Antibodies

To determine if there is an effect on aggregation when anti-CD40L antibody is cross-linked by an antibody specific for the Fc region of IgG, activated and resting platelets were treated with anti-CD40L antibody with or without anti-bFc as a cross-linking agent. One experiment was performed in which the effects of cross-linked anti-CD40L antibody were cross-titrated with varied amounts of ADP and anti-hFc (Table 5). Cross-linking of anti-CD40L antibody with 20 µg/mL or 6.66 µg/mL anti-hFc did not affect platelet aggregation (Table 5). However, increased aggregation was observed when anti-CD40L antibody was cross-linked with 2.22 µg/mL of anti-hFc (Table 5 compare lines 109 and 110). Such an enhancing effect was not observed when a lower concentration of ADP was used for activation (Table 5). Platelets were not affected by anti-CD40L antibody in the presence of normal human serum, which contains antibodies that are not expected to cross-link anti-CD40L antibody (Table 6). These results suggest that enhancement of platelet aggregation by anti-CD40L antibody cross-linked by antibodies is possible.

Anti-CD40L Antibody Cross-Linked by Soluble CD40 Ligand

Multiple concentrations of anti-CD40L antibody and sCD40L were evaluated in the platelet aggregation assay to determine whether anti-CD40L antibody cross-linked by sCD40L would enhance platelet aggregation. Based on the number of binding sites available on sCD40L and anti-CD40L antibody, anti-CD40L antibody would be maximally cross-linked when two molecules of trimeric sCD40L are bound to three molecules of divalent anti-CD40L antibody. By calculation, the weight/weight ratio for maximal cross-linking is theoretically 3.75 anti-CD40L antibody to 1 sCD40L. Several ratios in this range were tested, and 233 µg/mL anti-CD40L antibody and 30 µg/mL sCD40L was empirically found to be a condition for maximal cross-linking of anti-CD40L antibody. Ten-fold lower and ten-fold higher concentrations of anti-CD40L antibody were also evaluated with 30 µg/mL sCD40L. This test has been done using PRP prepared from ten healthy donors. Interestingly, enhanced aggregation occurred with platelets isolated from some, but not all, healthy donors.

Figure 3:
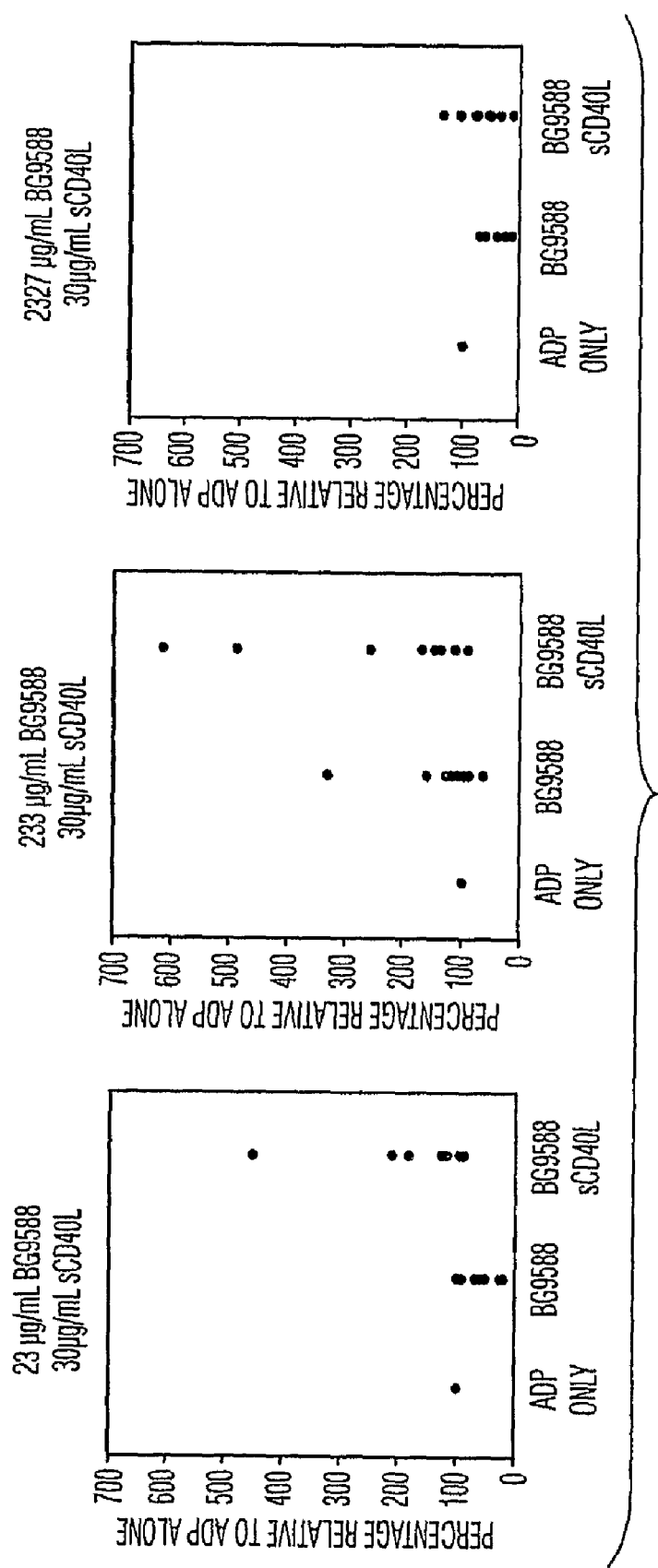
FIG. 3 shows that platelet aggregation is affected by complexes of anti-CD40L antibody and sCD40L. PRP was obtained from ten healthy donors. Anti-CD40L antibody and sCD40L were mixed at least 20 minutes prior to addition to the PRP. A titration was performed for each donor to determine an ADP concentration that produced suboptimal aggregation. Aggregation was induced using the sub-optimal ADP concentration. Each dot indicates the result from one person.
Figure 4:
FIG. 4 shows that platelet aggregation is specifically enhanced by complexes of anti-CD40L antibody and recombinant sCD40L. PRP was obtained from one healthy individual. Aggregation was induced with 0.75 µM ADP, which was determined to be suboptimal for this donor. Anti-CD40L antibody, hIgG, and aglycosylated anti-CD40L antibody were evaluated at 200 µg/mL and sCD40L at 30 µg/mL. Anti-CD40L antibody or hIgG was mixed with recombinant sCD40L for no less than 20 minutes prior to addition to the PRP-containing cuvette. Bars represent the means and standard deviations of two data points.

Platelet aggregation was induced by anti-CD40L antibody maximally cross-linked by sCD40L (FIG. 3). An aglycosylated version of anti-CD40L antibody cross-linked by sCD40L did not enhance platelet aggregation, indicating the effect is FcγRIIa-dependent (FIG. 4). Control human IgG (hIgG) and sCD40L together had no effect on platelet aggregation (FIG. 4).

TABLE 1

Effect of anti-CD40L antibody on ADP-Activated Platelets

| Sample # | BG9588 | ADP Concentration (µM) | % of Aggregation |
|---|---|---|---|
| 1 | | 20.00 | 73 |
| 2 | + | 20.00 | 72 |
| 3 | | 6.70 | 60 |
| 4 | + | 6.70 | 71 |
| 5 | | 2.00 | 25 |
| 6 | + | 2.00 | 21 |
| 7 | | 0.70 | 11 |
| 8 | + | 0.70 | 24 |
| 9 | | 0.37 | 12 |
| 10 | + | 0.37 | 15 |
| 11 | | 0.00 | 3 |
| 12 | + | 0.00 | 11 |

Anti-CD40L antibody does not induce the aggregation of resting platelets or affect the aggregation of ADP-activated platelets. PRP was placed in a cuvette and stirred with or without 5 µg/mL research-grade anti-CD40L antibody. ADP was added to the final concentrations listed. A four-minute aggregation tracing was generated for each sample and the percent of aggregation calculated.

TABLE 2

Effect of anti-CD40L antibody and IgG on ADP-Activated Platelets

| Sample # | BG9588 | Human IgG | ADP (µM) | % of Aggregation |
|---|---|---|---|---|
| 13 | | | 20.00 | 77 |
| 14 | | + | 20.00 | 89 |
| 15 | + | | 20.00 | 80 |
| 16 | | | 6.70 | 74 |
| 17 | | + | 6.70 | 75 |
| 18 | + | | 6.70 | 78 |
| 19 | | | 2.00 | 10 |
| 20 | | + | 2.00 | 12 |
| 21 | + | | 2.00 | 12 |
| 22 | | | 0.70 | 8 |
| 23 | | + | 0.70 | 11 |
| 24 | + | | 0.70 | 10 |
| 25 | | | 0.37 | 9 |
| 26 | | + | 0.37 | 10 |

TABLE 2-continued

Effect of anti-CD40L antibody and IgG on ADP-Activated Platelets

| Sample # | BG9588 | Human IgG | ADP (µM) | % of Aggregation |
|---|---|---|---|---|
| 27 | + | | 0.37 | 10 |
| 28 | | | 0.00 | 3 |

Anti-CD40L antibody and a control human IgG do not affect the aggregation of ADP-activated platelets. PRP was placed in a cuvette and stirred with or without 5 µg/mL of research-grade anti-CD40L antibody or human IgG. ADP was added to the final concentrations listed. A four-minute aggregation tracing was generated for each sample and the percent of aggregation calculated.

TABLE 3

Effect of anti-CD40L antibody and IgG on ADP-Activated Platelets

| Sample # | BG9588 | Human IgG | ADP (µM) | % of Aggregation |
|---|---|---|---|---|
| 29 | | | 0.00 | 1 |
| 30 | | + | 0.00 | 3 |
| 31 | + | | 0.00 | 3 |
| 32 | | | 20.00 | 70 |
| 33 | | + | 20.00 | 68 |
| 34 | + | | 20.00 | 68 |
| 35 | | | 10.00 | 64 |
| 36 | | + | 10.00 | 69 |
| 37 | + | | 10.00 | 69 |
| 38 | | | 5.00 | 72 |
| 39 | | + | 5.00 | 70 |
| 40 | + | | 5.00 | 67 |
| 41 | | | 2.50 | 65 |
| 42 | | + | 2.50 | 57 |
| 43 | + | | 2.50 | 62 |
| 44 | | | 1.25 | 13 |
| 45 | | + | 1.25 | 15 |
| 46 | + | | 1.25 | 12 |
| 47 | | | 0.60 | 10 |
| 48 | | + | 0.60 | 9 |
| 49 | + | | 0.60 | 10 |
| 50 | | | 0.30 | 10 |
| 51 | | + | 0.30 | 10 |
| 52 | + | | 0.30 | 10 |

Anti-CD40L antibody and a nonspecific human IgG do not induce the aggregation of resting platelets or affect the aggregation of ADP-activated platelets. PRP was placed in a cuvette and stirred with or without 5 µg/mL of research-grade anti-CD40L antibody or human IgG. ADP was added to the final concentrations listed. A four-minute aggregation tracing was generated for each sample and the percent of aggregation calculated.

TABLE 4

Effect of anti-CD40L antibody and CD40-Fc on ADP-Activated Platelets

| Sample # | BG9588 (µg/mL) | CD40Ig (µg/mL) | ADP (µM) | % of Aggregation |
|---|---|---|---|---|
| 53 | | | 0.00 | 2 |
| 54 | 20.00 | | 0.00 | 3 |
| 55 | 10.00 | | 0.00 | 3 |
| 56 | 5.00 | | 0.00 | 3 |
| 57 | 2.50 | | 0.00 | 5 |
| 58 | 1.25 | | 0.00 | 3 |
| 59 | | 20.00 | 0.00 | 3 |
| 60 | | 10.00 | 0.00 | 3 |

TABLE 4-continued

Effect of anti-CD40L antibody and CD40-Fc on ADP-Activated Platelets

| Sample # | BG9588 (µg/mL) | CD40Ig (µg/mL) | ADP (µM) | % of Aggregation |
|---|---|---|---|---|
| 61 | | 5.00 | 0.00 | 3 |
| 62 | | 2.50 | 0.00 | 3 |
| 63 | | 1.25 | 0.00 | 3 |
| 64 | | 0.63 | 0.00 | 3 |
| 65 | | | 20.00 | 84 |
| 66 | | | 5.00 | 79 |
| 67 | | 10.00 | 5.00 | 79 |
| 68 | | | 2.50 | 77 |
| 69 | | 10.00 | 2.50 | 81 |
| 70 | | | 1.25 | 61 |
| 71 | | 10.00 | 1.25 | 64 |
| 72 | | | 0.80 | 15 |
| 73 | | 10.00 | 0.60 | 16 |

The binding of anti-CD40L antibody or CD40-Fc to CD40L on the surface of activated platelets does not affect platelet aggregation. PRP was placed in a cuvette and stirred with or without research-grade anti-CD40L antibody or CD40-Fc at the concentrations listed. ADP was added to the final concentrations listed. A four-minute aggregation tracing was generated for each sample and the percent of aggregation calculated.

TABLE 5

Effect of Cross-linked anti-CD40L antibody on ADP-Activated Platelets

| Sample # | BG9588 | Anti-hFc (µg/mL) | ADP (µM) | % of Aggregation |
|---|---|---|---|---|
| 98 | | | 0.0 | 2 |
| 99 | | | 20.0 | 76 |
| 100 | | 20.00 | 0.0 | 3 |
| 101 | + | | 0.0 | 3 |
| 102 | + | 20.00 | 0.0 | 3 |
| 103 | | 20.00 | 1.0 | 73 |
| 104 | + | 20.00 | 1.0 | 83 |
| 105 | | 6.66 | 0.0 | 3 |
| 106 | | 6.66 | 1.0 | 80 |
| 107 | + | 6.66 | 1.0 | 84 |
| 108 | + | 2.22 | 0.0 | 3 |
| 109 | | 2.22 | 1.0 | 23 |
| 110 | + | 2.22 | 1.0 | 76 |
| 111 | + | 20.00 | 0.0 | 4 |
| 112 | | 20.00 | 0.5 | 6 |
| 113 | + | 20.00 | 0.5 | 8 |
| 114 | | 6.66 | 0.0 | 3 |
| 115 | | 6.66 | 0.5 | 8 |
| 116 | + | 6.66 | 0.5 | 8 |
| 117 | | 2.22 | 0.0 | 3 |
| 118 | | 2.22 | 0.5 | 7 |
| 119 | + | 2.22 | 0.5 | 8 |

The cross-linking of anti-CD40L antibody bound to CD40L on the surface of activated platelets may enhance aggregation under limited conditions. PRP was placed in a cuvette and stirred with or without research-grade anti-CD40L antibody at 2 µg/mL and/or anti-hFc at the concentrations listed. ADP was added to the final concentrations listed. A four-minute aggregation tracing was generated for each sample and the percent of aggregation calculated.

TABLE 6

Effect of Normal Human Serum on Resting Platelets

| Sample # | BG9588 | Serum (µg/mL) | % of Aggregation |
|---|---|---|---|
| 74 | | | 2 |
| 75 | | 1.0x | 8 |
| 76 | | 0.2x | 7 |
| 77 | | 0.04x | 5 |
| 78 | | 0.008x | 5 |
| 79 | | 0.0016x | 6 |
| 80 | | 0.00032x | 6 |
| 81 | + | 1.0x | 9 |
| 82 | + | 0.2x | 6 |
| 83 | + | 0.04x | 6 |
| 84 | + | 0.008x | 7 |
| 85 | + | 0.0016x | 6 |
| 86 | + | 0.00032x | 6 |

Normal human serum does not affect the aggregation of resting platelets. PRP was placed in a cuvette and stirred with or without research-grade anti-CD40L antibody at 2 pg/mL and/or normal human serum at the concentrations listed. A four-minute aggregation tracing was generated for each sample and the percent of aggregation calculated.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of assaying platelet aggregation comprising:
   contacting platelets with a platelet activating agent;
   contacting the activated platelets with a CD40L-binding moiety; and
   contacting the activated platelets with a cross-linking agent, wherein sedimented platelets is indicative of aggregation of the platelets.

2. The method of claim 1 wherein the platelet activating agent is selected from ADP, collagen, thrombin, thromboxane, neutrophil elastase, p-selectin, and convulxin.

3. The method of claim 1 wherein the platelet activating agent is ADP.

4. The method of claim 1 wherein the platelets are obtained from platelet rich plasma.

5. The method of claim 1 wherein the CD40L-binding moiety is an anti-CD40L antibody.

6. The method of claim 5 wherein the anti-CD40L antibody is hu5c8.

7. The method of claim 1 wherein the cross-linking agent is selected from sCD40L, anti-human IgG antibody, anti-hFc antibody, RF, Fc receptor-positive accessory cell, soluble protein A, and soluble human Fc receptor.

8. The method of claim 1 wherein the cross-linking agent is selected from sCD40L, anti-human IgG antibody, and anti-hFc antibody.

9. The method of claim 1 wherein the ratio of CD40L-binding moiety to cross-linking agent is 1:1000 to 1000:1.

10. The method of claim 1 wherein the ratio of CD40L-binding moiety to cross-linking agent is 1:500 to 500:1.

11. The method of claim 1 wherein the ratio of CD40L-binding moiety to cross-linking agent is 3:2.

12. A method of assaying platelet aggregation comprising:
    activating platelets with ADP;

contacting the activated platelets with an anti-CD40L antibody; and contacting the activated platelets with sCD40L or anti-hFc antibody, and wherein sedimented platelets is indicative of aggregation of the platelets.

13. A method of determining whether a human is susceptible to clotting upon administration of a CD40L-binding moiety comprising:

removing platelets from the human;

contacting the platelets with a platelet activating agent;

contacting the activated platelets with the CD40L-binding moiety; and contacting the activated platelets with a cross-linking agent, and determining the presence or absence of platelet aggregation, wherein 70% or greater platelet aggregation is indicative of susceptibility to clotting.

14. The method of claim 13 wherein the platelet activating agent is selected from ADP, collagen, thrombin, thromboxane, neutrophil elastase, p-selectin, and convulxin.

15. The method of claim 13 wherein the platelet activating agent is ADP.

16. The method of claim 13 wherein the platelets are obtained from platelet rich plasma.

17. The method of claim 13 wherein the CD40L-binding moiety is an anti-CD40L antibody.

18. The method of claim 17 wherein the anti-CD40L antibody is hu5c8.

19. The method of claim 13 wherein the cross-linking agent is selected from sCD40L, anti-human IgG antibody, anti-hFc antibody, RF, Fc receptor-positive accessory cell, soluble protein A, and soluble human Fc receptor.

20. The method of claim 13 wherein the cross-linking agent is selected from sCD40L, anti-human IgG antibody, and anti-hFc antibody.

21. The method of claim 13 wherein the ratio of CD40L-binding moiety to cross-linking agent is 1:1000 to 1000:1.

22. The method of claim 13 wherein the ratio of CD40L-binding moiety to cross-linking agent is 1:500 to 500:1.

23. The method of claim 13 wherein the ratio of CD40L-binding moiety to cross-linking agent is 3:2.

24. A method of determining whether a human is susceptible to clotting upon administration of an anti-CD40L antibody comprising:

removing platelets from the human;

activating the platelets with ADP;

contacting the activated platelets with the anti-CD40L antibody; and contacting the activated platelets with sCD40L or anti-hFc antibody, and determining the presence or absence of platelet aggregation, wherein 70% or greater platelet aggregation is indicative of susceptibility to clotting.

25. The method of claim 1, wherein the CD40L-binding moiety and the cross-linking agent are not a preformed immune complex.

26. The method of claim 12, wherein the anti-CD40L antibody and the sCD40L are not a preformed immune complex.

27. The method of claim 13, wherein the CD40L-binding moiety and the cross-linking agent are not a preformed immune complex.

28. The method of claim 24, wherein the anti-CD40L antibody and the sCD40L are not a preformed immune complex.

* * * * *